US012741007B2

(12) United States Patent
Choi et al.

(10) Patent No.: US 12,741,007 B2
(45) Date of Patent: Sep. 22, 2026

(54) COMPOSITION FOR PREVENTING, AMELIORATING, OR TREATING METABOLIC SYNDROMES INCLUDING OBESITY, DIABETES, HYPERLIPIDEMIA, AND FATTY LIVER

(71) Applicant: NUTRACORE CO., LTD., Gyeonggi-do (KR)

(72) Inventors: Beom-Rak Choi, Gyeonggi-do (KR); Sae-Kwang Ku, Daegu (KR); Hye-Rim Park, Gyeonggi-do (KR); Hyun Lee, Gyeonggi-do (KR)

(73) Assignee: NUTRACORE CO., LTD., Gyeonggi-do (KR)

( * ) Notice: Subject to any disclaimer, the term of this patent is extended or adjusted under 35 U.S.C. 154(b) by 746 days.

(21) Appl. No.: 17/766,787

(22) PCT Filed: Oct. 21, 2019

(86) PCT No.: PCT/KR2019/013826
§ 371 (c)(1),
(2) Date: Apr. 6, 2022

(87) PCT Pub. No.: WO2021/070999
PCT Pub. Date: Apr. 15, 2021

(65) Prior Publication Data

US 2024/0066090 A1 Feb. 29, 2024

(30) Foreign Application Priority Data

Oct. 8, 2019 (KR) ........................ 10-2019-0124286

(51) Int. Cl.

| | |
|---|---|
| ***A61K 36/899*** | (2006.01) |
| ***A61K 36/53*** | (2006.01) |
| ***A61P 1/16*** | (2006.01) |
| ***A61P 3/04*** | (2006.01) |
| ***A61P 3/06*** | (2006.01) |
| ***A61P 3/10*** | (2006.01) |

(52) U.S. Cl.
CPC ............ *A61K 36/899* (2013.01); *A61K 36/53* (2013.01); *A61P 1/16* (2018.01); *A61P 3/04* (2018.01); *A61P 3/06* (2018.01); *A61P 3/10* (2018.01)

(58) Field of Classification Search
CPC .. A61K 36/899; A61K 36/53; A61K 2236/00; A61K 31/216; A61K 31/4166; A61K 2300/00; A61P 1/16; A61P 3/04; A61P 3/06; A61P 3/10; A23V 2002/00; A23V 2200/3262; A23V 2200/328; A23V 2200/332; A23L 33/105
See application file for complete search history.

(56) References Cited

U.S. PATENT DOCUMENTS

2008/0187606 A1 8/2008 Kim et al.
2015/0037389 A1* 2/2015 Ragot .................... A23L 27/10 424/439

FOREIGN PATENT DOCUMENTS

| | | | |
|---|---|---|---|
| CN | 101254011 | A | 9/2008 |
| KR | 10-0645385 | B1 | 11/2006 |
| KR | 10-2008-0102058 | A | 11/2008 |
| KR | 10-1201628 | B1 | 11/2012 |
| WO | WO-2015/072678 | A1 | 5/2015 |
| YU | 49277 | B | 3/2005 |

OTHER PUBLICATIONS

Wang, K., and Zhao, J., Corn silk (*Zea mays* L.), a source of natural antioxidants with α-amylase, α-glucosidase, advanced glycation and diabetic nephropathy inhibitory activities, 2019 (online 2018), Biomedicine & Pharmacotherapy, 110:510-517, 8 pages. <https://doi.org/10.1016/j.biopha.2018.11.126>. (Year: 2018).*

Chung, M.J., et al., Anti-diabetic effects of lemon balm (*Melissa officinalis*) essential oil on glucose- and lipid-regulating enzymes in type 2 diabetic mice, 2010, British Journal of Nutrition, 104:180-188, 9 pages. <https://doi.org/10.1017/s0007114510001765>. (Year: 2010).*

Ramanauskiene, K., et al., Rosmarinic Acid and Melissa officinalis Extracts Differently Affect Glioblastoma Cells, 2016, Oxidative Medicine and Cellular Longevity, 1564257, 9 pages. <http://dx.doi.org/10.1155/2016/1564257>. (Year: 2016).*

Touiss et al., Rosmarinic acid-rich extract from *Ocimum basilicum* L. decreases hyperlipidemia in high fat diet-induced hyperlipidemic mice and prevents plasma lipid oxidation, Sep. 2019, Physiol Pharmacol 23(3):197-207, 11 pages. <https://dor.iscac/dor/20.1001.1.24765236.2019.23.3.8.2>. (Year: 2019).*

Medline Plus, Insulin Injection, 2017, 7 pages. <https://web.archive.org/web/20181106224344/https://medlineplus.gov/druginfo/meds/a682611.html> (Year: 2017).*

Go HK, et al. Antidiabetic Effects of Yam (*Dioscorea batatas*) and Its Active Constituent, Allantoin, in a Rat Model of Streptozotocin-Induced Diabetes. Nutrients. Oct. 15, 2015;7(10):8532-44, 13 pages. doi: 10.3390/nu7105411. PMID: 26501316; PMCID: PMC4632431. (Year: 2015).*

Weidner C, et al. Lemon balm extract causes potent antihyperglycemic and antihyperlipidemic effects in insulin-resistant obese mice. Mol Nutr Food Res. Apr. 2014;58(4):903-7, 5 pages. doi: 10.1002/mnfr.201300477. Epub Nov. 24, 2013. PMID: 24272914. (Year: 2013).*

(Continued)

*Primary Examiner* — Aaron J Kosar
*Assistant Examiner* — Jennifer Lynn Cain
(74) *Attorney, Agent, or Firm* — Harness, Dickey & Pierce, P.L.C.

(57) ABSTRACT

The present disclosure relates to a composition for preventing, improving or treating a metabolic syndrome such as obesity, diabetes, hyperlipidemia and fatty liver, comprising a combination of a Lemon balm extract and a corn silk extract as a natural extract as an active ingredient.

6 Claims, 6 Drawing Sheets

(56) References Cited

OTHER PUBLICATIONS

Maksimovic, Z., et al., Quantification of allantoin in various *Zea mays* L. hybrids by RP-HPLC with UV detection, 2004, Pharmazie, 59:524-527, 4 pages. <https://pubmed.ncbi.nlm.nih.gov/15296088/>. (Year: 2004).*

Pan, Yuxiang et al., Physicochemical Properties and Antidiabetic Effects, Carbohydrate Polymers, vol. 164, 2017, pp. 370-378.

Supplementary European Search Report from corresponding European Application No. 19948672.1, dated Aug. 3, 2023.

International Search Report from corresponding PCT Application No. PCT/KR2019/013826, dated Jun. 24, 2020.

* cited by examiner

COMPOSITION FOR PREVENTING, AMELIORATING, OR TREATING METABOLIC SYNDROMES INCLUDING OBESITY, DIABETES, HYPERLIPIDEMIA, AND FATTY LIVER

TECHNICAL FIELD

This application is a national phase application of PCT Application No. PCT/K R2019/013826, filed on Oct. 21, 2019, which claims priority to Korean Patent Application No. 10-2019-0124286, filed on Oct. 8, 2019. The entire disclosures of the applications identified in this paragraph are incorporated herein by references.

The present disclosure relates to a composition for preventing, improving or treating a metabolic syndrome including obesity, diabetes, hyperlipidemia and fatty liver, comprising a natural extract as an active ingredient.

BACKGROUND ART

Obesity is a cause of various lethal metabolic diseases such as cardiovascular disease, high blood pressure and Type II diabetes, and in case of obesity, adipocytes not only store lipids as a long-term energy source, but also secrete various adipokines involved in the metabolism and inflammation of adipocytes and non-adipocytes, causing chronic inflammation and related metabolic diseases such as insulin resistance. Recently, the incidence of metabolic syndromes, also known as Type II diabetes, is increasing worldwide due to obesity caused by lack of exercise along with a high-calorie diet, and it is predicted that the number of patients with metabolic syndromes will double, that is, nearly 300 million people by 2025. Obesity caused by abnormal local fat accumulation, such as abdominal obesity, provides various causes that may seriously induce arterial atheromatosis, such as high blood pressure, hyperlipidemia, blood clotting disorders, vascular inflammation, and insulin resistance with abnormal increase in insulin secretion, and ultimately, it becomes a factor in increasing the prevalence of fatal cardiovascular disease. Excessive intake of fatty acids causes the accumulation of triglyceride (TG) in various tissues, accompanied by an increase in lipolysis and an increase in circulating fatty acids in the blood, and causes insulin resistance in adipocytes, resulting fat accumulation in non-adipocytes in muscle, pancreas and liver. When insulin resistance is induced in adipocytes, excess fatty acid binding and carrier proteins lead to increase fatty acid uptake by non-adipocytes, and in particular, in case of muscle cells, it adversely affects insulin-mediated glucose metabolism, and at the same time, in the pancreas, long-term exposure to free fatty acids repeats a vicious cycle in which insulin secretion disorder is caused by the so-called lipotoxicity metabolism. In this case, a high concentration of free fatty acids is also accumulated in the liver, resulting in resistance to insulin, and a large amount of glucose begins to be liberated from the liver. Accumulation of TG in hepatocytes also causes non-alcoholic fatty liver disease (NAFLD), and causes fat accumulation of hepatocytes mainly responsible for glucose metabolism, secondarily resulting in steatohepatitis, and ultimately causes fibrosis by necrosis of hepatocytes. Therefore, the balance of fat synthesis and decomposition of hepatocytes has become an important therapeutic target that can inhibit induction of insulin resistance and NAFLD caused in case of metabolic syndrome.

Various metabolic syndrome therapeutic agents are currently being developed, and in recent years, appropriate control of oxidative stress, which is pointed out as a major cause of diabetes and related complications, along with proper blood glucose control, has emerged as the most important method for diabetes treatment, so the development of more effective α-glucosidase blocking agents or anti-oxidants with low side effects is being attempted.

Among them, metformin is well known as an AMPK activator as a representative oral biguanide-based anti-diabetic therapeutic agent. Metformin is the first drug used to treat overweight and obese Type II diabetes patients with normal renal function, and it is known as the only drug that can lower the onset of cardiovascular disease, one of the serious side effects of diabetes and can regulate the activity of enzymes related to secretion of pancreatic enzyme granules and liver glucose metabolism directly involved in digestion and decomposition of fat. Metformin is known as the most prescribed diabetes therapeutic agent worldwide currently. Metformin is mainly used as a type II diabetes therapeutic agent, but prescriptions for polycystic ovary syndrome and premature puberty are also increasing. On the other hand, side effects of metformin such as lactic acidosis due to renal disorder are also well known.

Therefore, there is a need for development of more effective alternative health functional foods and medicines derived from natural products with low side effects.

Numerous documents are referenced throughout the present description and citations thereof are indicated. The disclosures of the cited documents are incorporated herein by reference in their entirety to more clearly describe the level of the art to which the present disclosure pertains and the content of the present disclosure.

SUMMARY

Technical Problem

The present inventors have made research efforts to develop a natural substance exhibiting a therapeutic and inhibitory effect of a metabolic syndrome such as obesity, diabetes, hyperlipidemia and fatty liver without side effects, and as a result, have found that a combination of a Lemon balm extract and a corn silk extract has a significantly increased effect compared to the effects of each raw material in prevention, improvement and treatment of a metabolic syndrome, thereby completing the present disclosure.

Accordingly, an object of the present disclosure is to provide a composition for preventing, improving or treating a metabolic syndrome comprising the combination of a Lemon balm extract and a corn silk extract as an active ingredient.

Another object of the present disclosure is to provide a method for preventing, improving or treating the metabolic syndrome.

Other object and advantage of the present disclosure will become more apparent from the following detailed description of the invention, claims and drawings.

Technical Solution

One aspect of the present disclosure is to provide a composition for preventing, improving or treating one or more metabolic syndromes selected from the group consisting of obesity, diabetes, hyperlipidemia and fatty liver, comprising a combination of a Lemon balm extract and a corn silk extract as a natural extract as an active ingredient.

Lemon balm is a plant belonging to the family Labiatae and is native to Mediterranean basins such as Greece and Italy, and is also native to the American continent. Lemon balm is known to contain various active flavonoids (cynaroside, cosmosin, rhamnocitrin, isoquercitrin), terpene and triterpene acids (ursolic and oleanolic acid). The antiseptic, antiviral, antibacterial and antioxidant activity of the lemon balm extract has been reported so far, and the hepatoprotective effect of the lemon balm extract is also well known in a rat hyperlipidemia model.

Corn silk is a by-product of corn that is widely used around the world and has been used for a long time as one of the traditional medicines in the United States and France. Corn silk is known to have immune-active and digestive promoting effects.

The composition of the present disclosure comprises a combination of a lemon balm extract and a corn silk extract as an active ingredient, and the term used in the present disclosure, 'extract' has a meaning to include an extraction result obtained by juicing a raw material or treating an extraction solvent to a raw material, or a processed product obtained by formulating (for example, powdering) the same.

When the extract used in the composition of the present disclosure is obtained by treating an extraction solvent to a raw material, various extraction solvents may be used, and for example, a polar solvent or non-polar solvent may be used. As the polar solvent, (i) water, (ii) alcohol (preferably, methanol, ethanol, propanol, butanol, normal-propanol, isopropanol, normal-butanol, 1-pentanol, 2-butoxyethanol or ethylene glycol), (iii) acetic acid, (iv) DMF (dimethylformamide) and (v) DMSO (dimethyl sulfoxide) and the like may be used, and as the non-polar solvent, acetone, acetonitrile, ethyl acetate, methyl acetate, fluoroalkane, pentane, hexane, 2,2,4-trimethylpentane, decane, cyclohexane, cyclopentane, diisobutylene, 1-pentene, 1-chlorobutane, 1-chloropropane, o-xylene, diisopropyl ether, 2-chlropropane, toluene, 1-chloropropane, chlorobenzene, benzene, diethyl ether, diethyl sulfide, chloroform, dichloromethane, 1,2-dichloroethane, aniline, diethylamine, ether, carbon tetrachloride and THF, and the like may be used.

Preferably, the extract used in the present disclosure may be juiced a raw material, or extracted using any one selected from the group consisting of water, lower alcohol having 1 to 4 carbon atoms and mixtures thereof as an extraction solvent, but not limited thereto.

Furthermore, the term used in the present disclosure, 'extract' may have a meaning as a crude extract commonly used in the art as described above, but in a broad sense, also includes a fraction obtained by additionally fractionating the extract. In other words, the extracts obtained by juicing a raw material or using the aforementioned extraction solvent, as well as those obtained by additionally applying a purification process thereto. For example, a fraction obtained by passing the extract through an ultrafiltration membrane having a constant molecular weight cut-off value and also a fraction obtained by additionally conducted various purification methods, such as separation by various chromatography (produced for separation according to size, charge, hydrophobicity or affinity) are comprised in the extract of the present disclosure.

In addition, to the extract of the present disclosure, then, an additional process may be performed, for example, filtered or concentrated or dried to remove a solvent, or filtered, concentrated and dried all. Filtering may use filter paper or use a pressure reducing filter, and concentration may perform a pressure reducing concentrator and drying may perform spray drying or freeze drying to obtain an extract in a powder form.

According to one embodiment of the present disclosure, the lemon balm extract prepared as above may comprise rosmarinic acid of 35~70 mg/g, and the corn silk extract may comprise allantoin of 0.50~40 mg/g.

In the composition of the present disclosure, the aforementioned lemon balm extract and corn silk extract may be comprised in a mixture or complex. The mixture or complex is characterized by having a synergistic effect compared to each single substance of the lemon balm extract and corn silk extract. More specifically, the weight ratio of the lemon balm extract (LB) to the corn silk extract (CS) may be comprised at a weight ratio of 1:2 to 4:1 (LB:CS), and for example, may be comprised at a weight ratio of 1:1, 1:2, 2:1 or 4:1, and preferably, may be comprised at a weight ratio of 1:1 to 2:1 (LB:CS), but not limited thereto.

According to one embodiment, the composition of the present disclosure may be prepared by comprising preparing a lemon balm extract by juicing, or extracting the lemon balm shoot system (above-ground part) using any one selected from the group consisting of water, lower alcohol having 1 to 4 carbon atoms and mixtures thereof as an extraction solvent; preparing a corn silk extract by juicing corn silk or using any one selected from the group consisting of water, lower alcohol having 1 to 4 carbon atoms and mixtures thereof as an extraction solvent; and mixing the lemon balm extract and corn silk extract and stirring.

The composition of the present disclosure prepared as such may has one or more effects selected from the group consisting of body weight loss, blood glucose reduction, blood lipid reduction and fatty liver improvement, and thereby exhibits an effect of preventing, improving or treating a metabolic syndrome.

In addition, the present disclosure provides a pharmaceutical composition for preventing and treating a metabolic syndrome comprising a composition containing the active ingredient, which is formulated in a pharmaceutical unit administration form by adding a pharmaceutically acceptable carrier, excipient or diluent, or the like.

The "pharmaceutically acceptable" refers to a non-toxic composition which is physiologically acceptable and does not inhibit actions of active ingredients and commonly does not cause an allergic reaction such as gastrointestinal disorder and dizziness, or reaction similar thereto, when administered to a human.

The example of the carrier, excipient or diluent may include lactose, dextrose, sucrose, sorbitol, mannitol, xylitol, erythritol, maltitol, starch, acacia gum, alginate, gelatin, calcium phosphate, calcium silicate, cellulose, methyl cellulose, polyvinyl pyrrolidone, water, methylhydroxybenzoate, propylhydroxybenzoate, talc, magnesium stearate and mineral oil, and the like. In addition, the pharmaceutical composition may further comprise a filler, an anti-aggregative agent, a lubricant, a wetting agent, a flavoring agent, an emulsifier or a preservative, or the like.

The term "pharmaceutically effective dose" means an amount showing a higher response than that of a negative control group, and preferably, refers to an amount sufficient to exhibit the effect of preventing and/or treating a metabolic syndrome.

In addition, the pharmaceutical composition of the present disclosure may be formulated using a method known in the art so as to provide rapid, sustained or delayed release of an active ingredient after being administered into a mammal. The formulation may be a form of powder, granule, tablet, emulsion, syrup, aerosol, soft or hard gelatin capsule, sterile injection solution, and sterile powder.

The administration route of the pharmaceutical composition of the present disclosure is not limited thereto, but may be orally or parenterally administered. The parenteral administration route may include various routes, for example, dermal, intranasal, intraperitoneal, intramuscular, subcutaneous or intravenous ones. In addition, the pharmaceutical composition of the present disclosure may be administered in parallel with a known compound having an effect of preventing and/or treating a metabolic syndrome.

As another aspect, the present disclosure provides a food composition comprising any one composition of the above compositions.

The food composition of the present disclosure includes all processed forms of natural materials such as functional food, nutritional supplement, health food and food additives, and the like. The above type of food composition may be prepared in various forms according to a common method known in the art.

For example, as a health food, a lemon balm extract and a corn silk extract themselves may be prepared in a form of tea, juice and drink to drink, or may be consumed by granulation, encapsulation or pulverization. Moreover, in addition to the lemon balm extract and corn silk extract of the present disclosure, *Paeonia lactiflora, Cornus officinalis, Acanthopanax senticosus, Ganoderma lucidum, Fraxini cortex, Eucommia ulmoides, Angelica gigas, Gardeniae fructus, Astragalus membranaceus*, malt, trifoliate orange, vitamin C, fructo-oligosaccharide, stevioside, purified water, maltodextrin, and the like may be further comprised alone or in a mixture within the range that does not inhibit the purpose of the present disclosure, but other medicinal components and/or additives which may be further comprised in the food composition of the present disclosure are not limited to the above examples.

For example, the food composition according to the present disclosure may comprise thiamine (vitamin B1), riboflavin, ascorbic acid, niacin and vitamin B6 as an aqueous vitamin, and may comprise myristic acid, palmitic acid, stearic acid, oleic acid, linoleic acid, and the like as a fatty acid, and may comprise glycolic acid and acetic acid as a weak acid component, and may comprise aspartic acid, serine, glutamic acid, proline, glycine, alanine, cysteine, tyrosine, histidine, arginine, and the like, in addition to 8 kinds of essential amino acids such as threonine, valine, methionine, isoleucine, leucine, phenylalanine, tryptophane and lysine as an amino acid.

Effects

The composition of the present disclosure has one or more effects selected from the group consisting of body weight loss, blood glucose reduction, blood lipid reduction and fatty liver improvement, and thereby, it exhibits an effect of preventing, improving or treating a metabolic syndrome.

DETAILED DESCRIPTION

Hereinafter, the present disclosure will be described in more detail by examples. It will be obvious to those skilled in the art to which the present disclosure pertains that these examples are intended only to illustrate the present disclosure more specifically, but the scope of the present disclosure is not limited by these examples.

Example

I. Test Substance Preparation

1. Preparation of Lemon Balm Extract and Confirmation of Index Component

A lemon balm (LB; Lemon Balm, Lemon balm L) shoot system (above-ground part) was washed and pulverized, and then extracted at 60° C. for 2 hours using 60% ethanol (V/V) solvent to obtain a lemon balm extract. Then, it was filtered and concentrated, and then dried, to prepare a lemon balm extract to be used in the present disclosure as brown powder.

Figure 1:
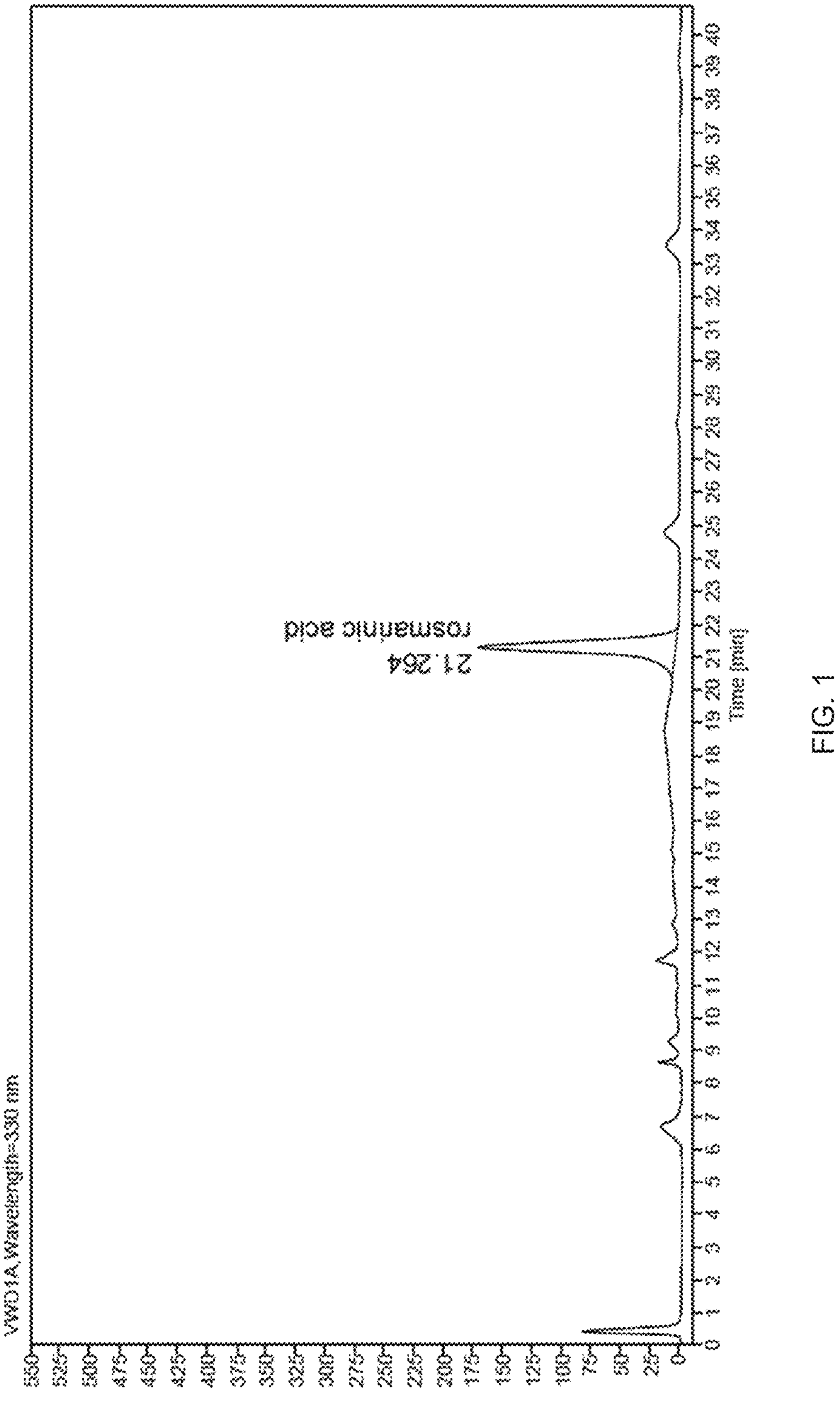
FIG. 1 shows the result of analyzing rosmarinic acid of a Lemon balm extract.

For the content of the rosmarinic acid in the lemon balm extract prepared above, it was separated using a high speed liquid chromatography method and then it was detected at a wavelength of 330 nm with a UV detector, and the result was shown in FIG. 1. As a result, the average rosmarinic acid content in the lemon balm extract was confirmed as 54.9 mg/g±30%.

2. Preparation of Corn Silk Extract and Confirmation of Index Component

Corn silk (CS; Corn Silk, *Maydis* stigma) washed and pulverized, and then extracted at 105° C. for 3 hours using water as an extraction solvent to obtain a corn silk extract. Then, it was filtered and concentrated, and then dried, to prepare a corn silk extract to be used in the present disclosure as dark brown powder.

Figure 2:
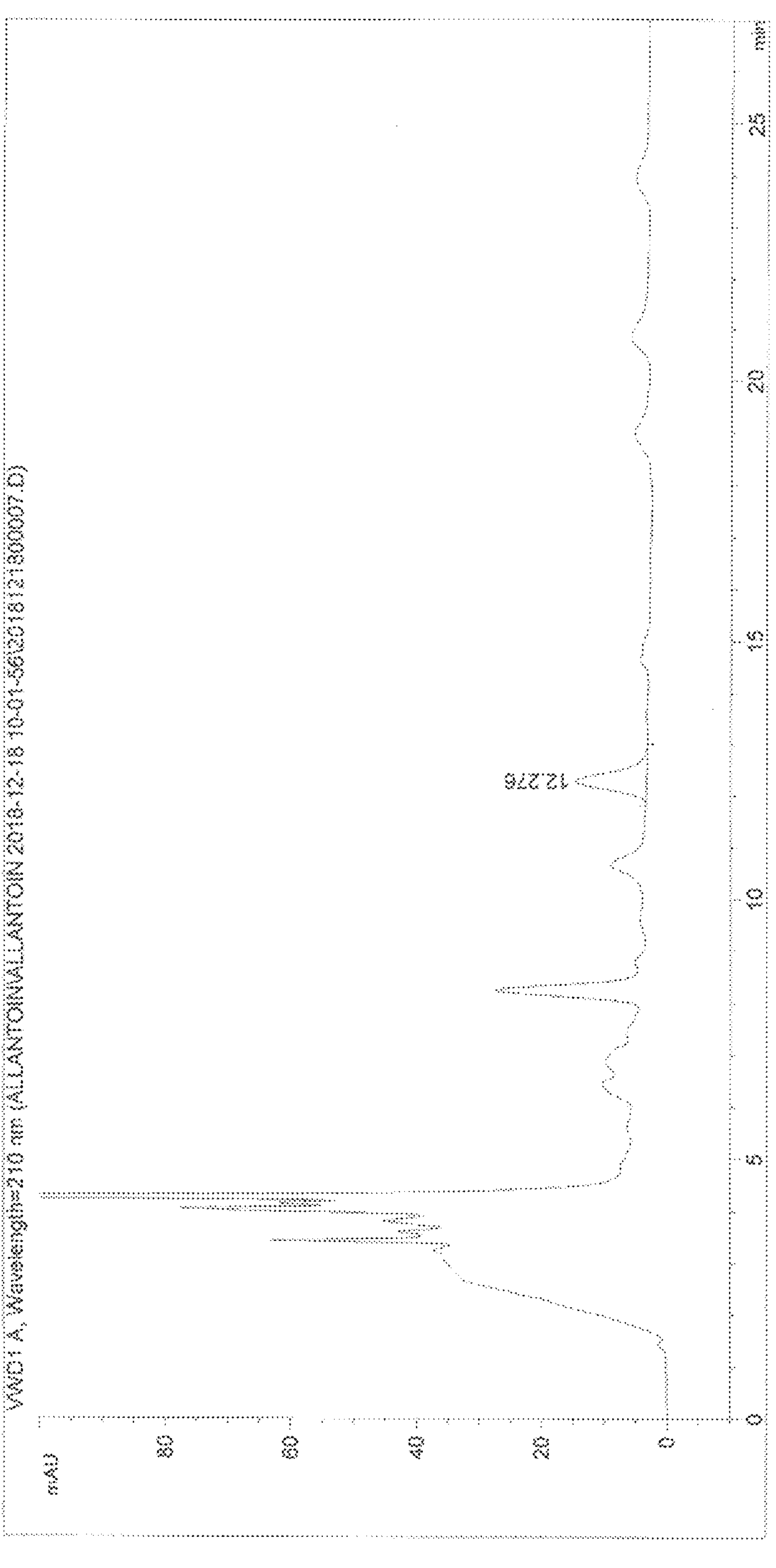
FIG. 2 shows the result of analyzing allantoin of a corn silk extract.

For the content of allantoin in the corn silk extract prepared above, it was separated using a high speed liquid chromatography method and then it was detected at a wavelength of 210 nm with a UV detector, and the result was shown in FIG. 2. As a result, the average allantoin content in the corn silk extract was confirmed as 0.75 mg/g±30%.

3. Preparation of Complex

The lemon balm extract prepared in the (1) and the corn silk extract prepared in the (2) were mixed at a weight ratio as Table 1 below to prepare complexes.

TABLE 1

| Lemon balm extract (LB):corn silk extract (CS) weight ratio | Lemon balm extract (LB) (g) | Corn silk extract (CS) (g) | Complex total weight (g) |
|---|---|---|---|
| 1:1 | 100 | 100 | 200 |
| 1:2 | 66 | 134 | 200 |
| 1:4 | 40 | 160 | 200 |
| 1:6 | 28 | 172 | 200 |
| 1:8 | 22 | 178 | 200 |
| 2:1 | 134 | 66 | 200 |
| 4:1 | 160 | 40 | 200 |
| 6:1 | 172 | 28 | 200 |
| 8:1 | 178 | 22 | 200 |

II. Effect Evaluation

1. Animal Model Establishment

The present inventors confirmed that the high fat diet (HFD) supply induced severe obesity even in mice which were rodents, and compared to normal pellet diet (NFD)-supplied mice, significant high blood glucose, insulin resistance, non-alcoholic steatohepatitis (NASH), mild diabetic nephropathy and hyperlipidemia were caused in the HFD inducing obesity mice. In other words, it was confirmed that the HFD supply could induce diabetic obesity similar to the human metabolic syndrome in ICR mice.

Various experimental animal models for development of a metabolic syndrome therapeutic agent were previously developed, but most of them induced very severe obesity and high blood glucose, so it was evaluated as suitable for evaluating the efficacy of an established therapeutic agent for diabetes, but not suitable for prevention or development of a functional food.

Thus, the present inventors established an experimental animal model using HFD resulting obesity and high blood glucose at an appropriate level for prevention of a metabolic syndrome including NAFLD and evaluation of the efficacy of the functional food.

Specifically, after acclimating total 200 6-week-old female ICR mice to a laboratory environment for 7 days, they were adapted to HFD (45% Kcal high fat diet) 1 week before the start of administration of the experimental substance, and then the experimental substance was administered, and in the normal control group, a general NFD (Normal pellet diet) was supplied by the same method.

As the experimental substance, the LB (lemon balm extract) and CS (corn silk extract) alone and 9 kinds of LB:CS complexes (LB:CS=1:1, 1:2, 1:4, 1:6, 1:8, 2:1, 4:1, 6:1 and 8:1 (g/g)) as described in Table 1 above were used. The administration dose of the experimental substance was equally set to 200 mg/kg in total based on the medicinal efficacy investigation research of the present inventors. The experimental substance was dissolved in sterile distilled water and orally administered.

2. Organ Weight and Adipocyte Size Change Measurement

The anti-obesity effect was evaluated on the basis of the change in the body weight, average feed intake, thickness of periovaric and abdominal wall accumulated fat using in live DEXA (dual-energy x-ray absorptionmetry) and average white adipocyte size, respectively. The administration dose of the experimental substance was equally set to 200 mg/kg in total, and Metformin was administered in an administration dose of 250 mg/kg, and the experimental result was shown in Table 2 below. The measurement value was represented by mean±SD for 8 mice.

TABLE 2

| | Items | | | |
|---|---|---|---|---|
| | Periovarian fat pads | | Abdominal wall fat pads | |
| Groups | Thickness (mm) | Adipocyte diameters (μm) | Thickness (mm) | Adipocyte diameters (μm) |
| Controls | | | | |
| Intact | 1.05 ± 0.22 | 32.75 ± 3.26 | 1.33 ± 0.36 | 37.68 ± 4.43 |
| HFD | 4.88 ± 0.81$^{a}$ | 93.82 ± 4.26$^{f}$ | 6.06 ± 1.17$^{f}$ | 113.50 ± 10.56$^{a}$ |
| Reference | | | | |
| Metformin | 2.83 ± 0.43$^{ab}$ | 48.12 ± 6.36$^{fg}$ | 2.99 ± 0.49$^{fg}$ | 64.49 ± 13.74$^{ab}$ |
| Test materials - 200 mg/kg | | | | |
| LB | 3.50 ± 0.31$^{ab}$ | 60.53 ± 6.62$^{fg}$ | 3.61 ± 0.39$^{fg}$ | 73.23 ± 5.97$^{ab}$ |
| CS | 3.76 ± 0.23$^{ab}$ | 66.74 ± 8.65$^{fg}$ | 3.85 ± 0.29$^{fg}$ | 80.22 ± 10.03$^{ab}$ |
| Mixed formula (LB:CS) - Totalized 200 mg/kg | | | | |
| 1:1 | 1.44 ± 0.42$^{bce}$ | 42.77 ± 4.98$^{fghi}$ | 1.96 ± 0.18$^{fghi}$ | 50.82 ± 12.39$^{abce}$ |
| 1:2 | 2.89 ± 0.31$^{abde}$ | 48.67 ± 6.40$^{fghi}$ | 3.02 ± 0.14$^{fghi}$ | 65.47 ± 3.55$^{abde}$ |
| 1:4 | 3.60 ± 0.37$^{ab}$ | 60.80 ± 10.56$^{fg}$ | 3.69 ± 0.29$^{fg}$ | 75.33 ± 7.97$^{ab}$ |
| 1:6 | 3.71 ± 0.63$^{ab}$ | 60.88 ± 9.52$^{fg}$ | 3.83 ± 0.31$^{fg}$ | 76.78 ± 10.71$^{ab}$ |
| 1:8 | 3.73 ± 0.39$^{ab}$ | 63.03 ± 12.25$^{fg}$ | 3.84 ± 0.31$^{fg}$ | 78.75 ± 11.85$^{ab}$ |
| 2:1 | 1.98 ± 0.60$^{abce}$ | 44.39 ± 6.17$^{fghi}$ | 2.18 ± 0.57$^{fghi}$ | 54.96 ± 6.24$^{abce}$ |
| 4:1 | 2.83 ± 0.34$^{abce}$ | 48.03 ± 4.46$^{fghi}$ | 2.98 ± 0.27$^{fghi}$ | 64.38 ± 4.38$^{abde}$ |
| 6:1 | 3.58 ± 0.51$^{ab}$ | 62.09 ± 8.65$^{fg}$ | 3.65 ± 0.31$^{fg}$ | 74.87 ± 10.56$^{ab}$ |
| 8:1 | 3.53 ± 0.72$^{ab}$ | 60.81 ± 9.32$^{fg}$ | 3.63 ± 0.37$^{fg}$ | 73.00 ± 13.53$^{ab}$ |

<Abbreviation description>

NFD = Normal pellet diet

HFD = 45% Kcal high fat diet

LB = Lemon balm (Lemon balm L) extract

CS = Corn silk (Stigma and style of corn, *Zea mays* L) extract $^{a}$p < 0.01, compared to intact control group by LSD test $^{b}$p < 0.01, compared to HFD control group by LSD test $^{c}$p < 0.01 and d p < 0.05, compared to LP single preparation by LSD test $^{e}$p < 0.01, compared to CS single preparation by LSD test $^{f}$p < 0.01, compared to intact control group by MW test $^{g}$p < 0.01, compared to HFD control group by MW test $^{h}$p < 0.01, compared to LB single preparation by MW test $^{i}$p < 0.01, compared to CS single preparation by MW test As the test result, in case of the HFD control group, a significant (p<0.01) increase of the periovaric and abdominal wall accumulated fat relative and absolute weight was recognized, compared to the normal control group, but in all the experimental substance administration groups including the CS single composition 200 mg/kg administration group, a significant (p<0.01) decrease of the periovaric and abdominal wall accumulated fat relative and absolute weight was shown, compared to the HFD control group, respectively, and in particular, in the LB:CS 1:1, 2:1, 4:1 and 1:2 (g/g) complex composition 200 mg/kg administration group, compared to each of the LB and CS single composition administration groups in the same dose, a significantly significant (p<0.01 or p<0.05) effect of inhibiting the HFD-induced increase of the periovaric and abdominal wall accumulated fat relative and absolute weight was shown. In the LB:CS 1:1 and 2:1 (g/g) complex composition 200 mg/kg administration group, a more excellent effect of inhibiting the increase of the periovaric and abdominal wall accumulated fat relative and absolute weight even than the metformin 250 mg/kg administration group was shown, and in the LB:CS 4:1 and 1:2 (g/g) complex composition 200 mg/kg administration group, an effect of inhibiting the HFD-induced increase of the periovaric and abdominal wall accumulated fat relative and absolute weight comparable to the metformin 250 mg/kg administration group was shown, respectively (Table 2).

3. Liver and Kidney Protective Effect Evaluation

In order to evaluate the liver protective effect, the change in the content of blood aspartate aminotransferase (AST), alanine aminotransferase (ALT), alkaline phosphatase (ALP), lactate dehydrogenase (LDH) and gamma-glutamyltransferase (GGT) was based, and in order to evaluate the kidney protective effect, the content of blood creatinine and urea nitrogen (BUN) was measured. The measured values were represented by mean±SD for 8 mice, and the result was shown in Table 3 below.

approved, respectively, and in particular, in the LB:CS 1:1, 2:1, 4:1 and 1:2 (g/g) complex composition 200 mg/kg administration group, compared to each of the LB and CS single composition administration groups in the same dose, a significantly significant (p<0.01 or p<0.05) HFD-induced blood AST, ALT, ALP, LDH and GGT content increase inhibitory effect was shown. In the LB:CS 1:1 and 2:1 (g/g) complex composition 200 mg/kg administration group, a more excellent effect of reducing the blood AST, ALT, ALP, LDH and GGT contents was shown even than the metformin 250 mg/kg administration group, and in the LB:CS 4:1 and 1:2 (g/g) 200 mg/kg administration group, an HFD-induced blood AST, ALT, ALP, LDH and GGT content increase inhibitory effect comparable to the metformin 250 mg/kg administration group was confirmed (Table 3).

For the BUN and creatinine contents, the HFD control group exhibited a significant (p<0.01) increase of the blood BUN and creatinine contents, respectively, compared to the normal control group, but, in all the experimental substance administration groups, a significant (p<0.01 or p<0.05) decrease of the blood BUN and creatinine contents was approved, respectively, compared to the HFD control group, and in particular, in the LB:CS 1:1, 2:1, 4:1 and 1:2 (g/g) complex composition 200 mg/kg administration group, a significantly significant (p<0.01 or p<0.05) HFD-induced blood BUN and creatinine content increase inhibitory effect was shown even than each of the LB and CS single composition administration groups in the same dose, and in the LB:CS 1:1 and 2:1 (g/g) complex composition 200 mg/kg administration group, a more excellent effect of reducing the blood BUN and creatinine contents even than the metformin 250 mg/kg administration group was shown, and in the LB:CS 4:1 and 1:2 (g/g) complex composition 200 mg/kg administration group, a HFD-induced blood BUN and creatinine content increase inhibitory effect comparable to the metformin 250 mg/kg administration group was shown (Table 3).

TABLE 3

| | Items | | | | | | |
|---|---|---|---|---|---|---|---|
| Groups | ALT (IU/L) | ALT (IU/L) | ALP (IU/L) | LDH (×10 IU/L) | GGT (IU/L) | BUN (mg/dl) | Creatinine (mg/dl) |
| Controls | | | | | | | |
| Intact | 69.13 ± 17.47 | 36.25 ± 10.94 | 76.88 ± 10.88 | 56.28 ± 19.15 | 2.88 ± 1.64 | 27.88 ± 11.08 | 0.44 ± 0.17 |
| HFD | 206.63 ± 15.32$^{a}$ | 153.88 ± 19.73$^{a}$ | 211.13 ± 27.32$^{a}$ | 333.27 ± 93.58$^{a}$ | 12.88 ± 1.96$^{a}$ | 101.75 ± 14.76$^{a}$ | 2.09 ± 0.45$^{g}$ |
| Reference | | | | | | | |
| Metformin | 140.38 ± 22.06$^{ac}$ | 105.00 ± 20.70$^{ac}$ | 134.50 ± 27.76$^{ac}$ | 156.13 ± 30.03$^{ac}$ | 6.75 ± 1.28$^{ac}$ | 51.88 ± 10.71$^{ac}$ | 1.13 ± 0.35$^{gh}$ |
| Test materials - 200 mg/kg | | | | | | | |
| LB | 168.75 ± 17.47$^{ac}$ | 121.50 ± 11.35$^{ac}$ | 163.00 ± 24.15$^{ac}$ | 204.51 ± 35.70$^{ac}$ | 8.88 ± 1.13$^{ac}$ | 73.00 ± 11.61$^{ac}$ | 1.39 ± 0.14$^{gh}$ |
| CS | 175.75 ± 18.94$^{ac}$ | 124.88 ± 9.67$^{ac}$ | 175.25 ± 22.21$^{ac}$ | 221.75 ± 42.98$^{ac}$ | 9.50 ± 1.20$^{ac}$ | 77.25 ± 10.65$^{ac}$ | 1.53 ± 0.17$^{gh}$ |
| Mixed formula (LB:CS) - Totalized 200 mg/kg | | | | | | | |
| 1:1 | 106.63 ± 17.00$^{adf}$ | 79.50 ± 17.01$^{acdf}$ | 107.38 ± 13.51$^{acdf}$ | 80.15 ± 12.88$^{cdf}$ | 4.25 ± 1.28$^{cdf}$ | 39.63 ± 8.86$^{bcdf}$ | 0.78 ± 0.24$^{ghjl}$ |
| 1:2 | 144.25 ± 12.99$^{acdf}$ | 103.75 ± 12.10$^{aef}$ | 134.50 ± 9.72$^{acdf}$ | 156.80 ± 24.71$^{acef}$ | 6.88 ± 1.25$^{acdf}$ | 54.00 ± 12.48$^{acdf}$ | 1.15 ± 0.30$^{ghkm}$ |
| 1:4 | 170.13 ± 16.23$^{ac}$ | 119.75 ± 13.57$^{ac}$ | 167.75 ± 16.65$^{ac}$ | 206.13 ± 52.30$^{ac}$ | 8.63 ± 2.26$^{ac}$ | 73.88 ± 11.73$^{ac}$ | 1.44 ± 0.17$^{gh}$ |
| 1:6 | 173.25 ± 12.29$^{ac}$ | 121.75 ± 11.78$^{ac}$ | 168.75 ± 17.81$^{ac}$ | 220.28 ± 31.23$^{ac}$ | 9.38 ± 1.19$^{ac}$ | 73.50 ± 12.12$^{ac}$ | 1.45 ± 0.35$^{gh}$ |
| 1:8 | 174.13 ± 18.07$^{ac}$ | 123.88 ± 12.99$^{ac}$ | 161.63 ± 14.23$^{ac}$ | 221.66 ± 33.27$^{ac}$ | 9.50 ± 1.93$^{ac}$ | 75.88 ± 12.55$^{ac}$ | 1.54 ± 0.27$^{gi}$ |
| 2:1 | 122.50 ± 14.12$^{adf}$ | 87.75 ± 13.12$^{acdf}$ | 116.88 ± 16.62$^{acdf}$ | 107.88 ± 25.49$^{bcdf}$ | 5.00 ± 1.51$^{acdf}$ | 44.38 ± 10.21$^{acdf}$ | 0.85 ± 0.13$^{ghjl}$ |
| 4:1 | 139.50 ± 17.92$^{acdf}$ | 101.63 ± 8.03$^{acdf}$ | 130.25 ± 13.24$^{acdf}$ | 153.17 ± 31.74$^{acdf}$ | 6.63 ± 1.06$^{acdf}$ | 52.13 ± 10.66$^{acdf}$ | 1.11 ± 0.22$^{ghkl}$ |
| 6:1 | 175.75 ± 16.02$^{ac}$ | 122.38 ± 13.27$^{ac}$ | 165.25 ± 11.59$^{ac}$ | 209.70 ± 34.67$^{ac}$ | 9.13 ± 1.25$^{ac}$ | 73.63 ± 12.45$^{ac}$ | 1.48 ± 0.33$^{gh}$ |
| 8:1 | 169.25 ± 19.16$^{ac}$ | 121.13 ± 13.59$^{ac}$ | 163.75 ± 17.08$^{ac}$ | 203.82 ± 39.15$^{ac}$ | 8.75 ± 1.49$^{ac}$ | 72.75 ± 12.83$^{ac}$ | 1.40 ± 0.27$^{gh}$ |

As the experimental result, in the HFD control group, a significant (p<0.01) increase of the blood AST, ALT, ALP, LDH and GGT contents was shown compared to the normal control group, but in all the experimental substance administration groups including the LB:CS 1:2 (g/g) complex composition 200 mg/kg administration group, a significant (p<0.01) decrease of the blood AST, ALT, ALP, LDH and GGT contents compared to the HFD control group was 4. Body Weight and Fat Density Evaluation In order to evaluate the anti-obesity effect, the change in the body weight was evaluated, and the result was shown in FIG. 3. In addition, the total body fat and abdominal fat density were measured using DEXA (live dual-energy x-ray absorptionmetry) and the result was shown in FIG. 4.

Figure 3:
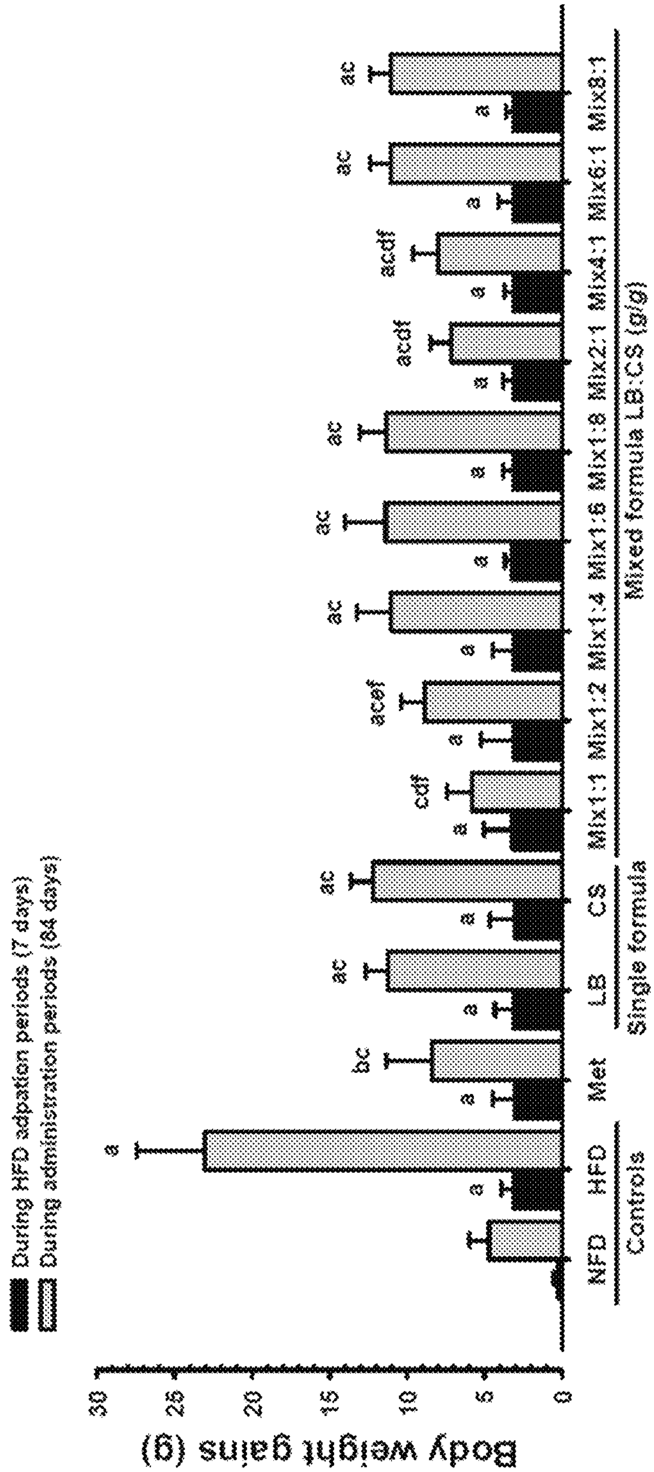
FIG. 3 shows the inhibitory activity of increasing body weight of the complex of the Lemon balm extract and corn silk extract.
Figure 4:
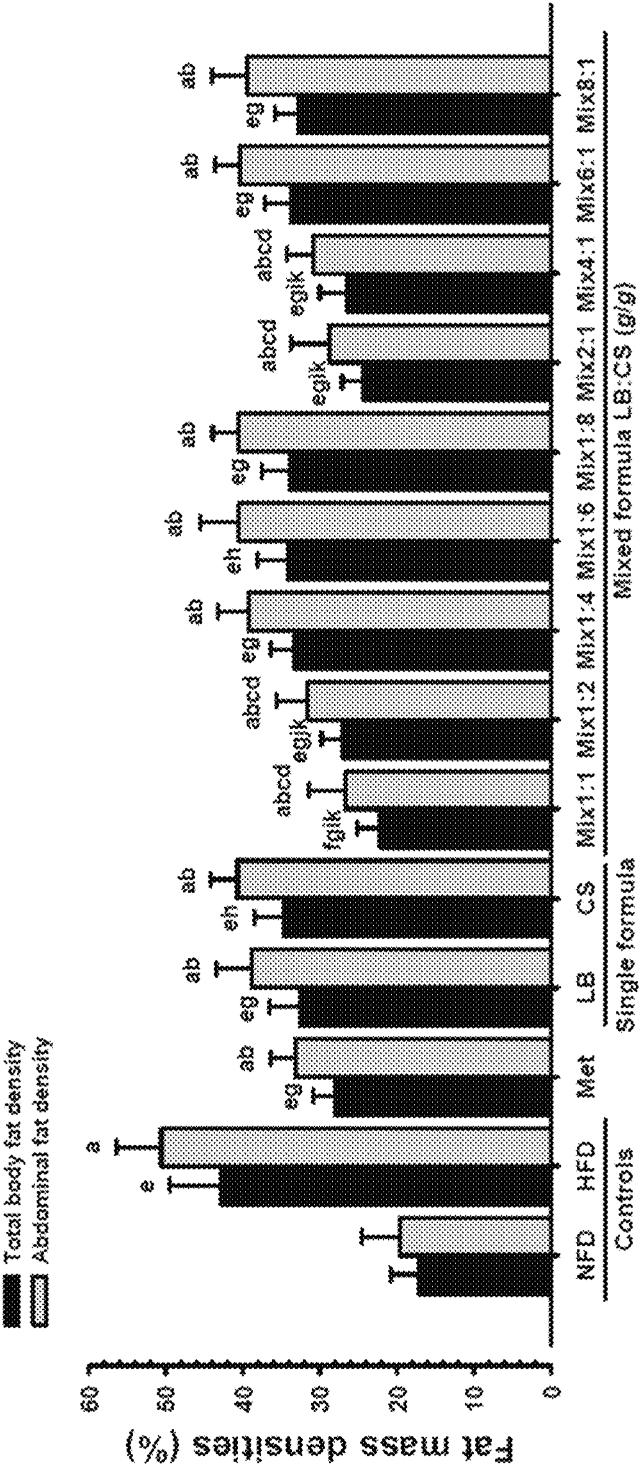
FIG. 4 shows the total body fat and abdominal fat density change.

In case of the body weight and fat density, in the HFD control group, a significant ($p<0.01$) increase of the body weight and fat density was approved in 7 days after the high fat diet supply, compared to the normal control group, and during the HFD adaptation period for 1 week and administration period of the experimental substance for 84 days, a significant ($p<0.01$) increase was also shown compared to the normal control group, respectively. On the other hand, in the LB:CS 1:2 (g/g) complex composition 200 mg/kg administration group, in 14 days after the start of administration, in the metformin 250 mg/kg, LB:CS 1:1, 1:6 and 2:1 (g/g) complex composition 200 mg/kg administration groups, in 21 days after the start of administration, in the LB:CS 4:1, 6:1 and 8:1 (g/g) complex composition 200 mg/kg administration group, in 28 days after the start of administration, and in the LB and CS single compositions and LB:CS 1:4 and 1:8 (g/g) complex composition 200 mg/kg administration group, in 35 days after the start of administration, a significant ($p<0.01$ or $p<0.05$) decrease of the body weight and fat density compared to the HFD control group began to be approved, respectively, and a significant ($p<0.01$) decrease of the body weight and fat density during the administration period of the experimental substance for 84 days compared to the HFD control group was also shown in order of LB:CS 1:1, 2:1 and 4:1 (g/g) complex composition 200 mg/kg, metformin 250 mg/kg, LB:CS 1:2, 1:4, 8:1, 6:1 (g/g) complex composition 200 mg/kg, LB single composition, LB:CS 1:8 and 1:6 (g/g) complex composition 200 mg/kg, and CS single composition 200 mg/kg administration groups, respectively. In particular, in the LB:CS 1:1, 2:1, 4:1 and 1:2 (g/g) complex composition 200 mg/kg administration groups, a significantly significant ($p<0.01$ or $p<0.05$) decrease of the body weight and fat density was shown in 35, 49, 70 and 70 days after the start of administration compared to the LB and CS single composition administration groups in the same dose, respectively, and a significantly significant ($p<0.01$ or $p<0.05$) decrease of the weight gain during the administration period of the experimental substance for 84 days was also shown compared to the LB and CS single composition 200 mg/kg administration groups. Overall, in the LB:CS 1:1 and 2:1 (g/g) complex composition 200 mg/kg administration groups, a more excellent body weight and fat density increase inhibitory effect was shown even than the metformin 250 mg/kg administration group, and in the LB:CS 4:1 and 1:2 (g/g) complex composition 200 mg/kg administration group, a HFD supply body weight and fat density increase inhibitory effect comparable to the metformin 250 mg/kg administration group was shown (FIG. 3 and FIG. 4).

5. Blood Insulin and Glycated Hemoglobin Amount Evaluation

Figure 5:
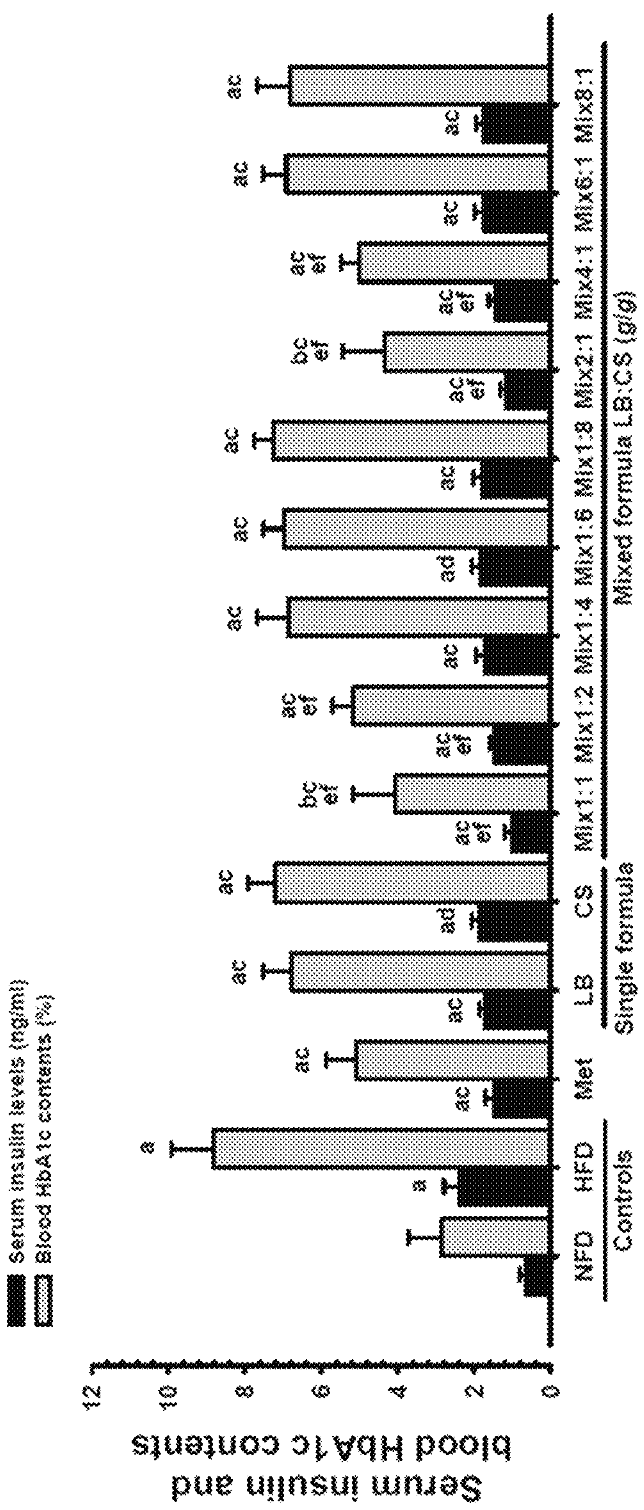
FIG. 5 shows the blood insulin and HbA1c change.

In order to evaluate the blood glucose lowering and anti-diabetic effect, the blood insulin and glycated hemoglobin (HbA1c) amount was measured, and the result was shown in FIG. 5.

HbA1c is produced from red blood cells exposed to long-term hyperglycemia, and is clinically used as an important indicator for long-term hyperglycemia. In addition, as type II diabetes progressed, an increase in the HbA1c content associated with long-term hyperglycemia along with an increase in the blood insulin content as a part of insulin resistance generally results.

As the result of the present experiment, in the HFD control group, a significant increase of the blood insulin and HbA1c contents was approved, and typical insulin resistant type II diabetes was induced. In all the experimental substance administration groups comprising the LB:CS 1:1 (g/g) complex composition 200 mg/kg administration group, it was observed that a change in the blood insulin and HbA1c contents by HFD supply was significantly inhibited, and in particular, in the LB:CS 1:1, 2:1, 4:1 and 1:2 (g/g) complex composition 200 mg/kg administration groups, compared to each of the LB and CS single composition administration groups in the same dose, a significantly significant decrease effect of the blood insulin and HbA1c contents was shown. In particular, in the LB:CS 1:1 and 2:1 (g/g) complex composition 200 mg/kg administration groups, a more excellent insulin resistant type II diabetes inhibitory effect was shown even than the metformin 250 mg/kg administration group, and in the LB:CS 4:1 and 1:2 (g/g) complex composition 200 mg/kg administration groups, an HFD-induced insulin resistant type II diabetes inhibitory effect comparable to the metformin 250 mg/kg administration group was shown, respectively. Accordingly, the LB:CS 1:1, 2:1, 4:1 and 1:2 (g/g) complex composition was determined as one of clear evidences which more synergistically increased the effect of improving blood glucose by pancreatic endocrine part control of LB and CS in HFD mice, and in particular, the LB:CS 1:1 and 2:1 (g/g) complex composition showing a more excellent inhibitory effect of HFD-induced insulin resistant type II diabetes than the metformin 250 mg/kg administration group was confirmed as the LB:CS optimal complex composition for improving diabetes.

6. Blood Lipid Content Evaluation

Figure 6:
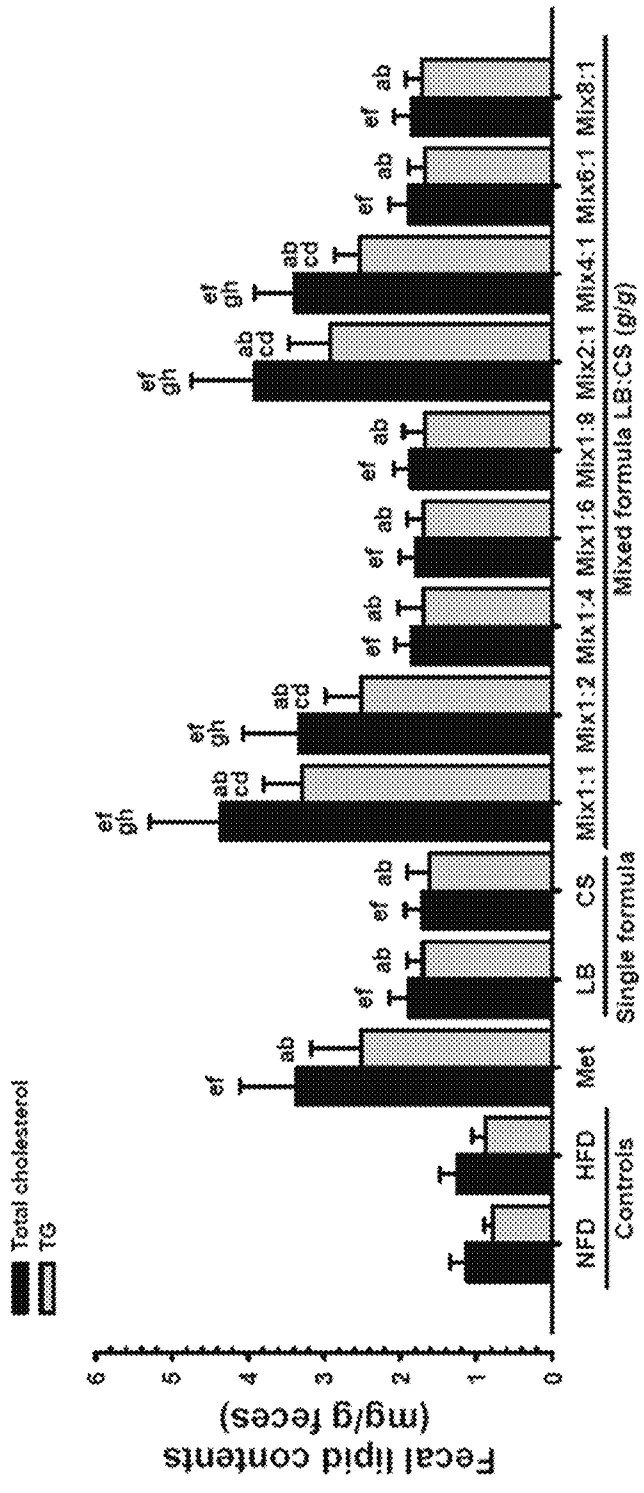
FIG. 6 shows the blood lipid content change.

As hyperglycemia continues, hyperlipidemia occurs as a complication, and in general, a total cholesterol and TG content increase during hyperlipidemia is caused. Therefore, in order to evaluate the anti-hyperlipidemic effect on the candidate substance, the blood total cholesterol and TG contents were measured, and the result was shown in FIG. 6.

As the result of the present experiment, in all the experimental substance administration groups including the LB:CS 1:2 (g/g) complex composition 200 mg/kg administration group, compared to the HFD control group, a significant decrease of the blood TG and total cholesterol contents was observed, respectively, and in particular, in the LB:CS 1:1, 2:1, 4:1 and 1:2 (g/g) complex composition 200 mg/kg administration groups, compared to each of the LB and CS single composition administration groups in the same dose, a significantly significant inhibitory effect of the blood lipid increase. In particular, in the LB:CS 1:1 and 2:1 (g/g) complex composition 200 mg/kg administration groups, an excellent HFD-induced hyperlipidemia inhibitory effect was shown, and in the LB:CS 4:1 and 1:2 (g/g) complex composition 200 mg/kg administration groups, an HFD-induced hyperlipidemia inhibitory effect comparable to the metformin 250 mg/kg administration group was shown, respectively. Thus, the LB:CS 1:1, 2:1, 4:1 and 1:2 (g/g) complex composition was determined as one of clear evidences which more synergistically increased the effect of inhibiting HFD-induced hyperlipidemia of LB and CS in HFD mice, and in particular, the LB:CS 1:1 and 2:1 (g/g) complex composition showing a more excellent inhibitory effect of HFD-induced hyperlipidemia than the metformin 250 mg/kg administration group was confirmed as the LB:CS optimal complex composition for improving obesity diabetes-related hyperlipidemia.

What is claimed is:

1. A method for reducing blood glucose and blood insulin levels, comprising:

administering a composition comprising a lemon balm extract and a corn silk extract as active ingredients to a patient in need thereof, wherein the weight ratio of the lemon balm extract (LB) to the corn silk extract (CS) is 1:2 to 4:1, wherein the lemon balm extract comprises 35 to 70 mg/g of rosmarinic acid, and wherein the corn silk extract comprises 0.50 to 40 mg/g of allantoin.

2. The method of claim 1, wherein the composition is a food composition, a pharmaceutical composition, or a health functional food.

3. The method of claim 1, wherein the composition produces one or more additional effects selected from the group consisting of body weight loss, blood lipid reduction, and fatty liver improvement.

4. The method of claim 1, wherein the weight ratio of the lemon balm extract to the corn silk extract is 1:1 to 2:1.

5. The method of claim 1, wherein the combination of the lemon balm extract and the corn silk extract produces a greater reduction of blood glucose and/or blood insulin levels relative to each individual extract.

6. The method of claim 1, wherein the lemon balm extract and the corn silk extract are juice or extracted with an extraction solvent selected from the group consisting of water, lower alcohol having 1 to 4 carbon atoms, and mixtures thereof.

* * * * *